United States Patent [19]

Vlock

[11] Patent Number: 4,583,982
[45] Date of Patent: Apr. 22, 1986

[54] FLUID DISPENSER

[76] Inventor: David G. Vlock, 12 Fifth Ave., New York, N.Y. 10011

[21] Appl. No.: 643,912

[22] Filed: Aug. 24, 1984

[51] Int. Cl.[4] .................................... A61M 35/00
[52] U.S. Cl. .................... 604/310; 222/575; 433/80; 604/289
[58] Field of Search ............ 604/289, 310; 433/80; 222/575

[56] References Cited

U.S. PATENT DOCUMENTS

| | | | |
|---|---|---|---|
| 1,513,342 | 10/1924 | Nitardy | 604/310 |
| 2,029,835 | 2/1936 | Reichle | 604/289 X |
| 2,180,533 | 11/1939 | Leffler | 604/289 |
| 2,520,605 | 8/1950 | Maynier | 604/289 X |
| 2,561,252 | 7/1951 | Waring | 604/289 X |
| 2,990,563 | 7/1961 | Davidson | 604/289 X |

*Primary Examiner*—Earl Nielsen
*Attorney, Agent, or Firm*—Lawrence Rosen

[57] ABSTRACT

A fluid dispensing device features a hand held tool having at least three fluid supporting prongs. The prongs are arranged in pyramidal fashion to form a fluid containing cradle at the apex. An exact amount of fluid is held in the cradle by surface tension forces. When the prongs are flexed, the surface tension forces are disrupted causing a discharge of the fluid to an exact area of a body surface.

12 Claims, 10 Drawing Figures

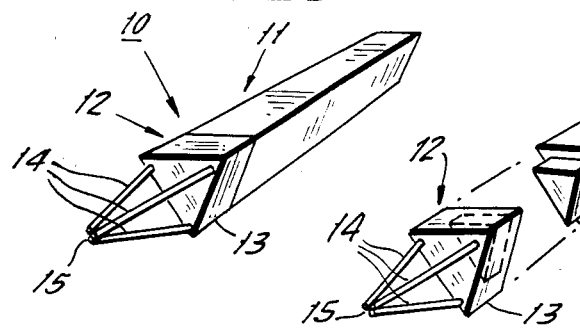
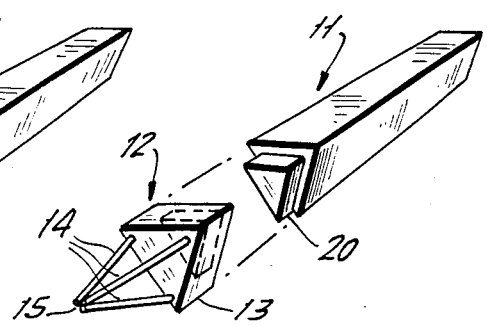
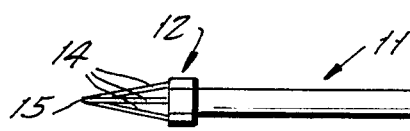
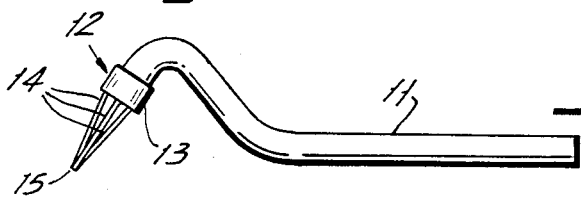
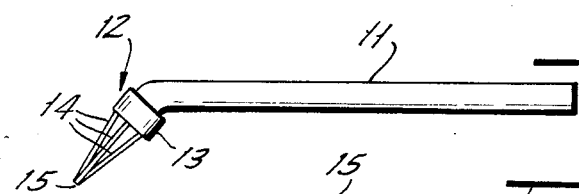
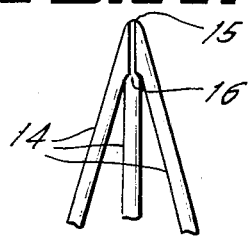
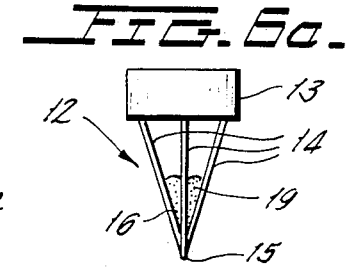
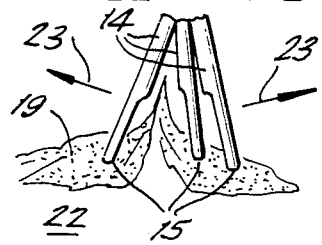
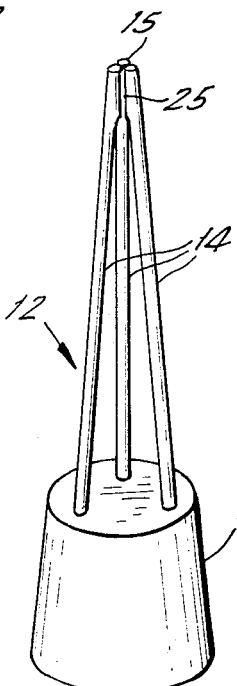

FLUID DISPENSER

FIELD OF THE INVENTION

The invention relates to a fluid dispensing device for placing a quantity of fluid upon a body surface, and more particularly to a hand-held tool for dispensing a fluid to a body surface in a precise manner.

BACKGROUND OF THE INVENTION

In dental, medical and surgical applications, it is often required to place a medicine or medicament upon a body surface, such as the gums, skin, eipthelium, cheek, or tongue. Often only a small amount of fluid is needed, particularly when applying caustics and astringents. These types of fluids require precise placement to the effected areas without spillage. Often exacting amounts are required in order to prevent dripping and run over into non-effected regions.

Hand-held dispensing tools have been invented that will extract fluid from a fluid source such as a vial or bottle, and which are capable of placing the fluid upon a body surface. Such devices are illustrated in U.S. Pat. No. 1,632,686; issued June 14, 1927 and U.S. Pat. No 1,586,302; issued May 25, 1926.

In both the above patents, a hand-held tool is described featuring a resilient tubular tip for carrying and dispensing fluids. While these hand-held devices accomplish placing small amounts of fluid upon various body surfaces, they cannot precisely extract a given quantity of fluid from a bottle or vial. The delivered fluid is always a little more or a little less than what may be required. Delivery of the fluid is not carefully controlled.

The present invention features a fluid dispensing tool that is designed to extract a precise amount of fluid from a container and then accurately deliver that fluid exactly to the effected region.

In addition, the invention is useful with a wide range of fluids having different viscosities. As such, the invention enjoys a universality and versatility not commonly found in similar devices.

SUMMARY OF THE INVENTION

The invention features a fluid dispenser having a handle portion supporting at least three spaced-apart, flexible prongs that meet at a pyramidal apex to form a fluid-containing cradle. The cradle holds a precise amount of fluid therein by means of the surface tension between the prongs and the fluid. The small cradle pocket formed at the apex of these prongs has a capillary channel disposed ahead of it, which terminates at the tip of the prongs. When the tip of the prongs are contacted to a body surface in question and slightly flexed, fluid will flow from the cradle through the capillary channel to this surface. Thus, a precise amount of fluid is accurately and precisely placed to the desired region.

The amount or quantity of the fluid held in the cradle pocket will depend upon the apex angle, the number of prongs and the choice of materials that influence the surface tension forces.

The prongs can be mounted on a truncated base, which in turn attaches to the handle by means of a key or a male/female connection. The base and the prongs are detachable from the handle, so that sanitary and aseptic conditions can be maintained between patients, i.e. new prongs are attached for each new use.

The cradle formed by the prongs will extract a precise quantity of fluid from a vial or bottle of fluid when immersed therein and subsequently removed.

It is an object of the invention to provide an improved fluid dispenser.

It is another object of this invention is to provide a fluid dispensing device to place accurately a precise quantity of fluid to a body surface.

These and other objects of the invention will be better understood and will become more apparent with reference to the following detailed description considered in conjunction with the accompanying drawings.

BRIEF DESCRIPTION OF THE DRAWINGS

FIG. 1 is a perspective view of the fluid dispensing device of this invention.

FIG. 1a is a perspective exploded view of the inventive device shown in FIG. 1.

FIGS. 2 through 4 illustrate respective embodiments of the device illustrated in FIG. 1.

FIG. 5 depicts an enlarged perspective view of the forward section of the device shown in FIG. 1.

FIG. 5a illustrates an enlarged view of the apex of the forward section shown in FIG. 5.

FIG. 5b shows an enlarged, exaggerated view of the apex of the forward section depicted in FIG. 5a in a fluid discharging mode.

FIGS. 6a and 6b depict schematic views of the apex of the forward section shown in FIG. 5 in a fluid supporting mode. FIG. 6a shows the fluid with a concave menescus and FIG. 6b depicts the fluid with a convex meniscus.

DETAILED DESCRIPTION OF THE INVENTION

Generally speaking, the invention pertains to a fluid dispensing device wherein precise amounts of fluid are extracted from a fluid source and then accurately placed upon a body surface.

Now referring to FIG. 1, the fluid dispensing device 10 of this invention is shown. The device 10 is comprised of a handle portion 11 and and a fluid carrying and discharging section 12. The fluid carrying and discharging section 12 includes a base 13 in which a number of spaced apart, flexible prongs 14 are affixed. The prongs 14 are arranged in the form of a pyramidal skeleton. Although three prongs 14 are illustrated, the device can function with more than three prongs.

However, at least three prongs are required to fulfill the unique fluid carrying capacity of the invention.

The prongs 14 form an apex 15 at their tip, wherein each prong 14 is closely adjacent but not attached to its neighboring prongs as may be seen in more detail in FIGS. 5 and 5a.

FIG. 5 depicts an enlarged view of the fluid carrying and discharging section 12 of FIG. 1.

FIG. 5a illustrates a further enlarged view of the apex 15 of the prongs 14.

The prongs 14 form a fluid carrying cradle 16 at the apex 15. The tips 17 of the prongs 14 do not touch each other, but rather form a narrow capillary channel 18 with its neighbor prongs directly ahead of the cradle 16.

When the apex 15 of the prongs 14 is immersed and removed from a fluid, a small, precise quantity of fluid 19 will be trapped in cradle 16, as is shown schematically in FIG. 6a. The fluid quantity 19 is trapped in cradle 16 by means of the surface tension between the fluid 19 and the prongs 14. In most cases, the fluid quantity 19 will form a concave meniscus between the prongs 14, as shown in FIG. 6a. However, with the use of hydrophobic materials for prongs 14, like teflon, the meniscus may actually be convex, as depicted in FIG. 6b.

Depending upon the number of prongs 14 used in the fluid section 12 and the types of materials and angles chosen for prongs 14, the quantity of fluid 19 can be varied to provide a precise amount of fluid extracted and carried in cradle 16.

The invention contemplates making fluid section 12 detachable from the handle 11, as shown in more detail in FIG. 1a. The Section 12 is made detachable for the reasons that different sections 12 can be used for different quantities of fluids. Also, sanitary and aseptic conditions would require a different section 12 for each patient, i.e. section 12 can be discarded after each use.

Section 12 can attach to handle 11 by means of a male-female connection, such as a triangular key 20 and mating triangular hole 21, as shown. After each use, section 12 can be removed from the handle 11, and a new fluid section 12 can be attached to handle 11.

The fluid quantity 19 can be precisely placed on a body surface, such as the skin or epithelium by touching the apex 15 of the prongs 14 to the body surface 22, as shown in the exaggerated enlarged view of FIG. 5b. The fluid quantity 19 will be drawn from the cradle 16 down the capillary channel 25 to flood the desired surface 22 by flexing the prongs 14 (arrows 23) to disrupt the surface tension forces holding the fluid 19 in cradle 16. The fluid will flow by capillary action in any desired direction, including antigravitationally and could possibly be used in outer space applications.

The shape of the handle 11 and the angle of section 12 can be varied, as shown in the alternate embodiments of FIGS. 2 through 4.

The shape of the handle 11 can be round as shown in FIGS. 2 and 3, or square or triangular, as illustrated in FIGS. 4 and 1, respectively. Different handle shapes may be more conveniently held in accordance with the preference of the user.

In addition, the mating angle between section 12 and handle 11 may be varied for placing fluid on surfaces that are not easily accessible. FIG. 3 illustrates a curved handle 11 and an angled section 12. FIG. 4 depicts an angled section 12 with a straight handle 11.

In keeping with the design or shape of the handle 11, the base 13 of section 12 can be a truncated cone, or a square or triangular prism.

The prongs 14 can be made of plastics or other inert materials that are flexible, sturdy, and chemically resistant.

The handle and base portions of the device 10 can also be made from plastics that are strong and sturdy.

Where it is desired to sterilize the instrument, such plastics must be temperature resistant. Other materials such as titanium will provide inertness, strength and temperature and chemical resistance.

Having thus described the invention, what is desired to be protected by Letters Patent is presented by the subsequent appended claims.

What is claimed is:

1. A fluid dispenser for applying a fluid to a body surface in a precise fashion, comprising a handle portion supporting at least three spaced-apart, prongs that meet at a pyramidal apex to form a fluid containing cradle, said fluid held in said cradle by surface tension, said fluid dispenser discharging said fluid from said cradle upon contact of said prongs to said body surface.

2. The fluid dispenser of claim 1, wherein said prongs form a capillary channel at said apex, said fluid being dischargeable from said cradle through said capillary channel when said prongs contact said body surface.

3. The fluid dispenser of claim 1, wherein said prongs are detachable from said handle portion.

4. The fluid dispenser of claim 1, wherein said prongs are mounted upon a base supported by said handle portion.

5. The fluid dispenser of claim 4, wherein said base is detachable from said handle portion.

6. The fluid dispenser of claim 4, wherein said base is truncated.

7. The fluid dispenser of claim 4, wherein said base is keyed to said handle portion.

8. The fluid dispenser of claim 1, wherein said prongs are flexible, and are caused to flex upon contact with said body surface.

9. The fluid dispenser of claim 1, wherein said cradle will extract fluid from a fluid source upon emersion into said fluid source.

10. The fluid dispenser of claim 9, wherein said cradle holds and discharges a given quantity of fluid.

11. A fluid dispenser for applying a fluid to a body surface, comprising a handle supporting at least three, spaced-apart prongs that meet at a pyramidal apex to form a fluid containing cradle, said prongs being separated by a capillary channel disposed ahead of said cradle for the discharge of fluid from said cradle.

12. A fluid dispenser for applying a fluid to a body surface, comprising a handle portion supporting at least three, spaced-apart, flexible prongs that meet at a pyramidal apex to form a fluid containing cradle, said flexible prongs being separated by a capillary channel disposed ahead of said cradle for discharging fluid from said cradle when said prongs are caused to flex upon contact with said body surface.

* * * * *